United States Patent
Liao et al.

(10) Patent No.: US 11,214,577 B2
(45) Date of Patent: Jan. 4, 2022

(54) MORPHINANS USEFUL FOR TREATING MEDICAL DISORDERS

(71) Applicant: Humanwell Pharmaceutical US, Ballwin, MO (US)

(72) Inventors: Subo Liao, Ballwin, MO (US); Jun Yang, Ballwin, MO (US); Jie Li, Ballwin, MO (US); Wentao Du, Ballwin, MO (US); Lie Li, Ballwin, MO (US); Jinliang Lv, Ballwin, MO (US); Zongquan Liao, Ballwin, MO (US); Hao Zhou, Ballwin, MO (US); Tianpeng Xie, Ballwin, MO (US); Jianbo Yu, Ballwin, MO (US)

(73) Assignee: Humanwell Pharmaceutical US, Ballwin, MO (US)

( * ) Notice: Subject to any disclaimer, the term of this patent is extended or adjusted under 35 U.S.C. 154(b) by 0 days.

(21) Appl. No.: 16/834,449

(22) Filed: Mar. 30, 2020

(65) Prior Publication Data
US 2020/0308185 A1 Oct. 1, 2020

Related U.S. Application Data

(60) Provisional application No. 62/826,188, filed on Mar. 29, 2019.

(51) Int. Cl.
*C07D 491/08* (2006.01)

(52) U.S. Cl.
CPC ................... *C07D 491/08* (2013.01)

(58) Field of Classification Search
CPC .................................... C07D 491/08
USPC ........................................ 514/282
See application file for complete search history.

(56) References Cited

U.S. PATENT DOCUMENTS

| 6,147,084 | A  | * | 11/2000 | Nagase | A61K 31/485 |
|---|---|---|---|---|---|
| | | | | | 514/282 |
| 6,277,859 | B1 | * | 8/2001 | Nagase | A61P 9/00 |
| | | | | | 514/282 |
| 6,323,212 | B1 | | 11/2001 | Nagase | |
| 6,372,755 | B2 | | 4/2002 | Hanamura | |
| 6,583,151 | B2 | | 6/2003 | Nagase | |
| 8,420,662 | B2 | | 4/2013 | Takaki | |
| 8,637,539 | B2 | | 1/2014 | Nagase | |
| 8,829,019 | B2 | | 9/2014 | Ohta | |
| 9,006,262 | B2 | * | 4/2015 | Suzuki | A61P 7/06 |
| | | | | | 514/289 |
| 10,131,672 | B2 | * | 11/2018 | Kobayashi | C07D 489/02 |
| 2006/0063792 | A1 | | 3/2006 | Dolle | |
| 2007/0197573 | A1 | | 8/2007 | Sadee | |
| 2011/0015219 | A1 | | 1/2011 | Trawick | |
| 2014/0336212 | A1 | | 11/2014 | Sadee et al. | |
| 2015/0335638 | A1 | | 11/2015 | Trawick et al. | |

FOREIGN PATENT DOCUMENTS

| JP | 2000053572 | | 2/2000 | |
| WO | WO-9315081 A1 | * | 8/1993 | ............. A61P 43/00 |
| WO | WO-9503307 A1 | * | 2/1995 | ........... A61K 31/485 |
| WO | 2006034039 A2 | | 3/2006 | |
| WO | 20200205735 A1 | | 10/2020 | |

OTHER PUBLICATIONS

Law, Molecular mechanisms and regulation of opioid receptor signaling. Annu Rev Pharmacol Toxicol 2000; 40 389-430.
Cowan, Kappa opioid agonists suppress chloroquine-induced scratching in mice. Eur J. Pharmacol 2004; 502, 233-7.
Gottschlich, Novel developments with selective non-peptidic kappa-opioid receptor agonists. Exp Opinion Investigational drugs. 1997; 6:1351-68.
Wadenberg, , A review of the properties of spiradoline: a potent and selective kappa-opioid receptor agonist. CNS Drug Rev. 2003, Summer, 9(2): 187-98.
Walsh, Strain EC, Abreu M.E. Bigelow G.E. Enadoline , a selective kappa opioid agonist: comparison with butorphanol and hydromorphone in humans. Psychopharmacology 2001, 15, 151-162.
DeHaven-Hudkins,Peripherally restricted opioid agonists as novel analgesic agents Curr Pharm Des 2004; 10:743-57.
International Search Report and Written Opinion dated Jun. 30, 2020 in related International Application No. PCT/US2020/025717, 8 pages.

\* cited by examiner

*Primary Examiner* — Rita J Desai
(74) *Attorney, Agent, or Firm* — Polsinelli PC

(57) ABSTRACT

The present invention related to novel morphinans, compositions comprising the novel morphinans, and their uses as agonists of the kappa opioid receptor.

12 Claims, 1 Drawing Sheet

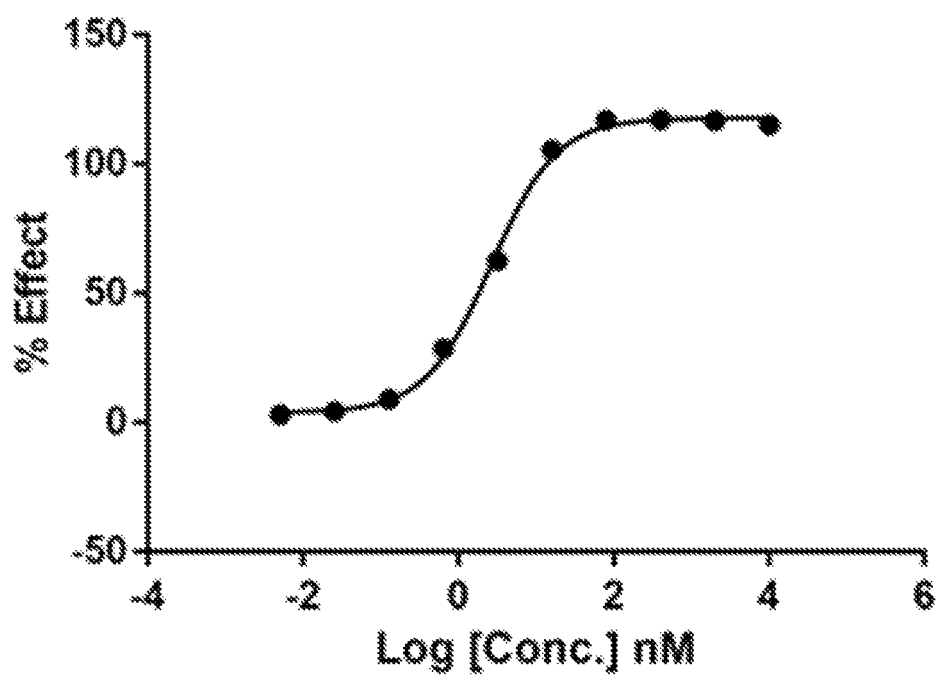

MORPHINANS USEFUL FOR TREATING MEDICAL DISORDERS

CROSS-REFERENCE TO RELATED APPLICATION

This application claims benefit of U.S. Provisional Patent Application No. 62/826,188, which was filed in the U.S. Patent and Trademark Office on Mar. 29, 2019, all of which is incorporated herein by reference in its entirety for all purposes.

FIELD OF THE INVENTION

The present disclosure generally relates to novel morphinans useful in treating medical disorders.

BACKGROUND OF THE INVENTION

Kappa opioid receptors (KORs) exist in many parts of the body such as brain, spinal cord, and on central and peripheral terminals. KORs play an important role in signal transduction; like other two opioid receptors mu opioid receptors (MORs) and delta opioid receptors (DORs). Agonist-induced activation of KORs leads to the inhibition of adenylyl cyclase and calcium channel activity while stimulation of the potassium channel activities (see Law P Y, Wong Y H, Loh H H; "Molecular mechanisms and regulation of opioid receptor signaling" Annu Rev Pharmacol Toxicol 2000; 40: 389-430).

A variety of physiological processes are related to the activation of KORs such as analgesia, anti-pruritic actives (see Irian S, Cowan A. "Kappa opioid agonists suppress chloroquine-induced scratching in mice." Eur J. Pharmacol 2004; 502, 233-7) and diuresis (see Barber A, Gottschlich R. "Novel developments with selective non-peptidic kappa-opioid receptor agonists." Exp Opinion Investigational drugs. 1997; 6: 1351-68; DeHaven-Hudkins D L, Dolls R. E.; "Peripherally restricted opioid agonists as novel analgesic agents." Curr Pharm Des 2004; 10:743-57), inflammation, immune system modulation, et al. which offer great potentials for KORs to treat many medical disorder such as pain, depression, autoimmune disorders, and neurological diseases.

Many KORs selective agonists were designed as potential analgesics in an attempt to avoid of side effects associated with traditional opioid analgesics such as respiratory depression, dependence, addiction, and constipation. Some KORs have been tested in clinical trial but failed due to side effects like diuresis, sedation, and dysphoria, et al or lack of efficacy. Some examples include spiradoline mesylate (see Wadenberg M L, "A review of the properties of spiradoline: a potent and selective kappa-opioid receptor agonist." CNS Drug Rev. 2003, Summer, 9(2): 187-98), enadoline for potential analgesics (see Walsh S L., Strain E C, Abreu M. E. Bigelow G. E.; "Enadoline, a selective kappa opioid agonist: comparison with butorphanol and hydromorphone in humans." Psychopharmacology 2001, 157, 151-162), and ADL-10-0101.

CR-845 is another KORs agonist currently in the clinical trials for analgesics and anti-pruritic agents. TRK-820 was originally developed as potential analgesics but achieved success as anti-pruritic reagents and received regulatory approval in Japan.

KORs agonists are also developed for other indications such fedotozine as potential therapeutics for irritable bowel syndrome and dyspepsia, and asimadoline as potential treatment for irritable bowel syndrome and functional dyspepsia.

What is needed is a novel opioid kappa agonists which has potential therapeutic value to treat various KORs-related medical disorder without side effects.

BRIEF DESCRIPTION OF FIGURE

FIG. 1 is a response curve of compound 5a measuring the % effect versus the log of the concentration (nM) which affords the $EC_{50}$.

SUMMARY OF THE INVENTION

Among the various aspects of the present disclosure is compound comprising Formula (I):

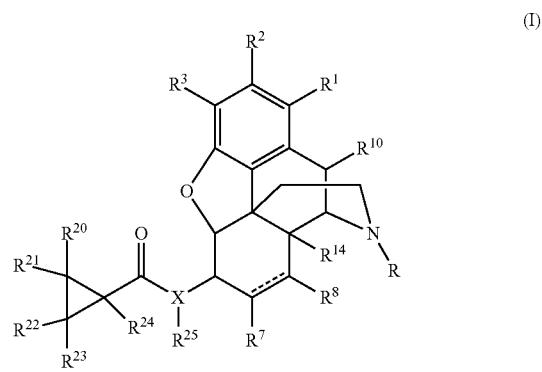

wherein:
R is hydrogen, alkyl, substituted alkyl, cycloalkyl, alkyl cycloalkyl, alkenyl, substituted alkenyl, aryl, substitute aryl, alkylaryl, or substituted alkylaryl;
$R^1$ and $R^2$ independently are hydrogen, halogen, hydroxy, alkoxy, aryloxy, amino, amine, nitro, alkyl, or substituted alkyl;
$R^3$ is hydrogen, hydroxy, alkyoxy, aryloxy, halogen, amino, or thiol;
$R^7$ and $R^8$ independently are hydrogen, halogen, hydroxy, alkoxy, amino, amine, thiol, alkyl, or substituted alkyl;
$R^{10}$ is hydrogen, hydroxy, alkyoxy, keto, ether, ester, amino, or amine;
$R^{14}$ is hydrogen, hydroxy, or alkoxy;
$R^{20}$, $R^{21}$, $R^{22}$, $R^{23}$, and $R^{24}$ independently are hydrogen, halogen, alkyl, substituted alkyl, alkenyl, substituted alkynyl, aryl, substituted aryl, alkylaryl, substituted alkylaryl, heterocycle, substituted heterocycle, alkylheterocycle, or substituted alkylheterocycle;
$R^{25}$ is hydrogen, halogen, alkyl, substituted alkyl, alkenyl, substituted alkynyl, aryl, substituted aryl, alkylaryl, substituted alkylaryl, heterocycle, substituted heterocycle, alkylheterocycle, substituted alkylheterocycle, or absent;
X is nitrogen, oxygen, or sulfur; and
the dashed line represents an optional double bond.

In another aspect, the present disclosure provides pharmaceutical compositions comprising any of the compounds of Formula (I) and at least one pharmaceutically acceptable excipient.

In still another aspect, the present disclosure provides a method for treating a kappa opioid receptor-related disease or disorder. The method comprises administrating the composition comprising a compound of Formula (I) to an individual in need thereof.

Other features and iterations of the invention are described in more detail below.

DETAILED DESCRIPTION OF THE INVENTION

The present disclosure provides compounds comprising Formula (I), pharmaceutical compositions comprising any of the compounds of Formula (I) and at least one pharmaceutically acceptable excipient, and methods for treating a kappa opioid receptor-related disease or disorder. The compounds disclosed herein have been shown to be selective to the kappa opioid receptor and, as such, would provide a therapy for treating kappa opioid receptor-related diseases or disorders.

(I) Compounds Comprising Formula (I)

One aspect of the present disclosure provides compounds comprising Formula (I):

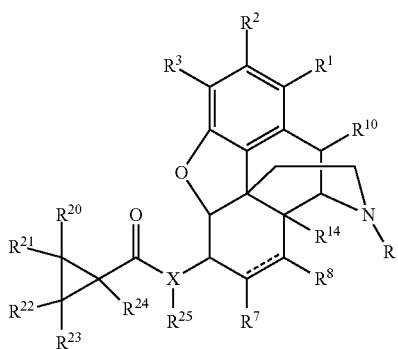

wherein:
R is hydrogen, alkyl, substituted alkyl, cycloalkyl, alkyl cycloalkyl, alkenyl, substituted alkenyl, aryl, substitute aryl, alkylaryl, or substituted alkylaryl;
$R^1$ and $R^2$ independently are hydrogen, halogen, hydroxy, alkoxy, aryloxy, amino, amine, nitro, alkyl, or substituted alkyl;
$R^3$ is hydrogen, hydroxy, alkyoxy, aryloxy, halogen, amino, or thiol;
$R^7$ and $R^8$ independently are hydrogen, halogen, hydroxy, alkoxy, amino, amine, thiol, alkyl, or substituted alkyl;
$R^{10}$ is hydrogen, hydroxy, alkyoxy, keto, ether, ester, amino, or amine;
$R^{14}$ is hydrogen, hydroxy, or alkoxy;
$R^{20}$, $R^{21}$, $R^{22}$, $R^{23}$, and $R^{24}$ independently are hydrogen, halogen, alkyl, substituted alkyl, alkenyl, substituted alkynyl, aryl, substituted aryl, alkylaryl, substituted alkylaryl, heterocycle, substituted heterocycle, alkylheterocycle, or substituted alkylheterocycle;
$R^{25}$ is hydrogen, halogen, alkyl, substituted alkyl, alkenyl, substituted alkynyl, aryl, substituted aryl, alkylaryl, substituted alkylaryl, heterocycle, substituted heterocycle, alkylheterocycle, substituted alkylheterocycle, or absent;
X is nitrogen, oxygen, or sulfur; and
the dashed line represents an optional double bond.

In some embodiments, R may be hydrogen, alkyl, substituted alkyl, alkylcycloalkyl, alkenyl, substituted alkenyl, aryl, substitute aryl, alkylaryl, or substituted alkylaryl. In other embodiments, R may be hydrogen, methyl, allyl, cyclopropylmethyl, or cyclobutylmethyl. In specific embodiments, R may be cyclopropylmethyl or 1-hydroxylcycloproylmethyl.

In some embodiments, $R^1$ and $R^2$ independently may be hydrogen, halogen, hydroxy, alkoxy, aryloxy, amino, amine, nitro, alkyl, or substituted alkyl. In other embodiments, $R^1$ and $R^2$ independently may be hydrogen, hydroxyl, methoxy, methyl, or chloride. In specific embodiments, $R^1$ and $R^2$ may be hydrogen.

In some embodiments, $R^3$ may be hydrogen, hydroxy, alkyoxy, aryloxy, halogen, amino, or thiol. In other embodiments, $R^3$ may be hydroxy, methoxy, ethoxy, isopropoxy, or phenoxy. In specific embodiments, $R^3$ may be hydroxyl.

In some embodiments, $R^7$ and $R^8$ independently may be hydrogen, halogen, hydroxy, alkoxy, amino, amine, thiol, alkyl, or substituted alkyl. In other embodiments, $R^7$ and $R^8$ independently may be hydrogen, chloro, hydroxyl, amino, methoxy, or methyl. In specific embodiments, $R^7$ and $R^8$ may be hydrogen.

In some embodiments, $R^{10}$ may be hydrogen, hydroxy, alkyoxy, keto, ether, ester, amino, or amine. In other embodiments, $R^{10}$ may be hydrogen, hydroxy, methoxy, or amine. In specific embodiments, $R^{10}$ may be hydrogen.

In some embodiments, $R^{14}$ may be hydrogen, hydroxy, or alkoxy. In other embodiments, $R^{14}$ may be hydrogen or hydroxy. In specific embodiments, $R^{14}$ may be hydrogen.

In some embodiments, $R^{20}$, $R^{21}$, $R^{22}$, $R^{23}$, and $R^{24}$ independently may be hydrogen, halogen, alkyl, substituted alkyl, alkenyl, substituted alkynyl, aryl, substituted aryl, alkylaryl, substituted alkylaryl, heterocycle, substituted heterocycle, alkylheterocycle, or substituted alkylheterocycle wherein heterocycle is chosen from furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, thienyl, phenol, or imidazopyridyl. In other embodiments, at least one of $R^{20}$, $R^{21}$, $R^{22}$, $R^{23}$, and $R^{24}$ may be aryl, substituted aryl, alkylaryl, substituted alkylaryl, heterocycle, substituted heterocycle, alkylheterocycle, or substituted alkylheterocycle wherein the heterocycle is defined above. In another embodiment, one of $R^{20}$, $R^{21}$, $R^{22}$, and $R^{23}$ is a heterocycle or substituted heterocycle and the rest are chosen from hydrogen or halogen, and $R^{24}$ may be hydrogen wherein heterocycle is defined above. In specific embodiments, $R^{20}$, $R^{21}$, $R^{23}$, and $R^{24}$ may be hydrogen and $R^{22}$ may be furyl, thienyl, or 4-hydroxyphenol.

In another embodiment, $R^{25}$ may be hydrogen, halogen, alkyl, substituted alkyl, alkenyl, substituted alkynyl, aryl, substituted aryl, alkylaryl, substituted alkylaryl, heterocycle, substituted heterocycle, alkylheterocycle, substituted alkylheterocycle, or absent wherein the heterocycle is defined above. In some embodiments, $R^{25}$ may be hydrogen, alkyl, or substituted alkyl. In an alternate embodiment, $R^{25}$ may be $C_1$-$C_4$ alkyl or substituted $C_1$-$C_4$ alkyl. In specific embodiments, $R^{25}$ may be methyl.

In one embodiment, X may be nitrogen, oxygen, or sulfur. In other embodiment, X may be nitrogen or oxygen. In specific embodiments, X may be nitrogen.

In other embodiments, the dashed line may represent an optional double bond. In specific embodiments, the dashed line may represent a single bond.

In exemplary embodiments, R may be cyclopropylmethyl or 1-hydroxylcyclopropylmethyl; $R^3$ may be hydroxyl; $R^1$, $R^2$, $R^7$, $R^8$, $R^{10}$, $R^{14}$, $R^{20}$, $R^{21}$, $R^{23}$, and $R^{24}$ may be hydrogen; $R^{22}$ may be furyl, thienyl, or 4-hydroxyphenyl; and $R^{25}$ may be methyl as shown below.

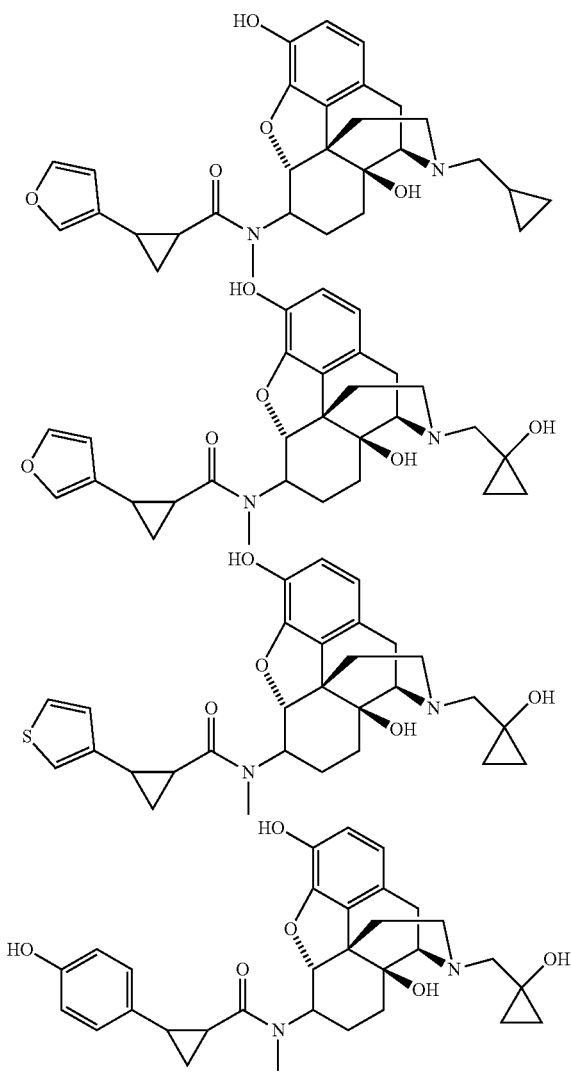

In general, the morphinans and normorphinans detailed herein include any compound comprising a morphinan structure as diagrammed below, wherein R is alkyl, substituted alkyl, alkylcycloalkyl, alkenyl, substituted alkenyl, aryl, substitute aryl, alkylaryl, or substituted alkylaryl in morphinans, and R is hydrogen in normorphinans. For the purposes of illustration, the ring atoms of the core morphinan structure are numbered as shown below:

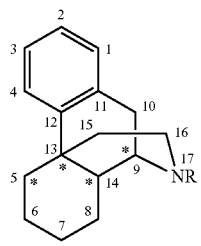

Morphinan compounds have asymmetric centers. In particular, the core morphinan compound may have at least four chiral carbons (designated by asterisks in the diagram above); namely, C-5, C-13, C-14, and C-9.

The compound comprising Formula (I) may have a (−) or a (+) orientation with respect to the rotation of polarized light. More specifically, each chiral center of the morphinans or normorphinans may have an R or an S configuration. The compounds described herein may have at least four chiral centers, namely carbons C-5, C-9, C-13, and C-14. At each chiral center, the stereochemistry at the carbon atom is independently R or S. The configuration of C-5, C-9, C-13, and C-14, respectively, may be RRRR, RRRS, RRSR, RSRR, SRRR, RRSS, RSSR, SSRR, SRRS, SRSR, RSRS, RSSS, SRSS, SSRS, SSSR, or SSSS, provided that the C-15 and C-16 atoms are both on the alpha face of the molecule or both on the beta face of the molecule.

The group on C-6 of the compounds comprising Formula (I) exist as alpha isomers or beta isomers. The alpha isomer to beta isomer ratio of any of these compounds may be from about 0:100 to about 100:0.

The carbons on the cyclopropyl ring of the compounds comprising Formula (I) exist in either an R or S configuration.

The compound comprising Formula (I) may be a free form or a salt. When the compound is in a salt form, the salt is preferably a pharmaceutically acceptable salt. Pharmaceutically acceptable salts may include, without limitation, hydrochloride, hydrobromide, phosphate, sulfate, methanesulfonate, acetate, formate, tartaric acid, bitartrate, stearate, phthalate, hydroiodide, lactate, monohydrate, mucate, nitrate, phosphate, salicylate, phenylpropionate, isobutyrate, hypophosphite, maleic, malic, citrate, isocitrate, succinate, lactate, gluconate, glucuronate, pyruvate, oxalate, fumarate, propionate, aspartate, glutamate, benzoate, terephthalate, and the like. In other embodiments, the pharmaceutically acceptable salt includes an alkaline or alkaline earth metal ion salt. In particular, sodium, potassium or other pharmaceutically acceptable inorganic salts are used. The salt forms may be amorphous or in various polymeric forms including hydrates, or solvates with alcohols or other solvents.

(II) Pharmaceutical Compositions

The disclosure also provides a pharmaceutical composition comprising a compound comprising Formula (I) and at least one pharmaceutically acceptable excipient.

(a) Compounds Comprising Formula (I)

The compounds comprising Formula (I) are described in more detail in Section (I).

(b) Excipient

A pharmaceutical composition of the disclosure comprises at least one pharmaceutically acceptable excipient. Non-limiting examples of suitable excipients may include diluents, binders, fillers, buffering agents, pH modifying agents, disintegrants, dispersing agents, stabilizers, preservatives, and coloring agents. The amount and types of excipients may be selected according to known principles of pharmaceutical science.

In one embodiment, the excipient may include at least one diluent. Non-limiting examples of suitable diluents may include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose.

In another embodiment, the excipient may comprise a binder. Suitable binders may include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

In another embodiment, the excipient may include a filler. Suitable fillers may include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may comprise a buffering agent. Buffers may include phosphates, carbonates, citrates, and the like. Representative examples of suitable buffering agents may include, but are not limited to, MOPS, HEPES, TAPS, Bicine, Tricine, TES, PIPES, MES, Tris buffers or buffered saline salts (e.g., Tris buffered saline or phosphate buffered saline).

In various embodiments, the excipient may include a pH modifier. By way of non-limiting example, the pH modifying agent may be sodium carbonate or sodium bicarbonate.

In another alternate embodiment, the excipient may also include a preservative. Non-limiting examples of suitable preservatives may include antioxidants, such as alpha-tocopherol or ascorbate, or EDTA (ethylenediaminetetraacetic acid), EGTA (ethylene glycol tetraacetic acid), BHA (butylated hydroxyanisole), BHT (butylated hydroxytoluene), and the like.

In a further embodiment, the excipient may include a disintegrant. Suitable disintegrants may include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

In yet another embodiment, the excipient may include a dispersion enhancer. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In a further embodiment, the excipient may include a lubricant. Non-limiting examples of suitable lubricants may include minerals such as talc or silica; and fats such as vegetable stearin, magnesium stearate, or stearic acid.

In still another embodiment, it may be desirable to provide a coloring agent. Suitable color additives may include, but are not limited to, food, drug and cosmetic colors (FD&C), drug and cosmetic colors (D&C), or external drug and cosmetic colors (Ext. D&C).

The weight fraction of the excipient(s) in the composition may be about 99% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The pharmaceutical composition may be mixed with one or more excipients to form a solid, liquid, or cream dosage form. Methods of formulating a solid, liquid, or cream dosage form are known in the art.

(III) Processes to Prepare Compounds Comprising Formula (I)

In yet another aspect, the present disclosure provides processes to prepare compounds comprising Formula (I). The processes commences by converting the 6-keto position on the morphinan or nor-morphinan to the corresponding amino, hydroxyl, or thiol group in either the alpha isomer or beta isomer. These processes are disclosed and known in the arts.

The next step in the process comprises contacting the amino, hydroxyl, or thiol group with an acyl group to form an amide, an ester, or a thioester. These processes may utilize an acyl coupling agent, a proton acceptor, and at least one solvent. These processes may be conducted at various temperatures and pressures. Numerous processes are known by the skilled artisan and disclosed in the arts.

(IV) Methods of Treating Kappa Opioid Receptor-Related Disease or Disorder

In still another aspect, the present disclosure provides a method of treating a kappa opioid receptor-related disease or disorder, wherein the method comprises administering to a subject in need thereof a pharmaceutical composition comprising a compound of Formula (I).

Without being bound to any theory, compounds comprising Formula (I) are thought to mediate the kappa opioid receptor activity primarily as an agonist. The binding at this site is thought to treat pain, pruritis, addiction, depression, stress, anxiety, autoimmune disorders, mycocardial infarction, inflammation, edemia, emetic, or neurological diseases.

The compounds may be administered to the subject by a variety of routes. For example, a compound comprising Formula (I) may be administered orally via a solid or liquid dosage form (tablet, gel cap, time release capsule powder, solution, or suspension in aqueous or non-aqueous liquid), parenterally (i.e., subcutaneously, intradermally, intravenously, (i.e., as a solution, suspension or emulsion in a carrier), intramuscularly, intracranially, or intraperitoneally), or topically (i.e., transdermally or transmucosally, including, but not limited to buccal, rectal, vaginal and sublingual). In one embodiment, the compounds may be administered in saline or with a pharmaceutically acceptable excipient as described above. The compound may be administered as primary therapy, or as adjunct therapy, either following local intervention (surgery, radiation, local chemotherapy) or in conjunction with at least one other chemotherapeutic agent.

Suitable subjects may include, without limit, humans, as well as companion animals such as cats, dogs, rodents, and horses; research animals such as rabbits, sheep, pigs, dogs, primates, mice, rats and other rodents; agricultural animals such as cows, cattle, pigs, goats, sheep, horses, deer, chickens and other fowl; zoo animals; and primates such as chimpanzees, monkeys, and gorillas. The subject can be of any age without limitation. In a preferred embodiment, the subject may be a human.

Generally, the compound comprising Formula (I) will be administered in a therapeutically effective amount which includes prophylactic amounts or lower dosages for example, when combined with another agent. As used herein, "an effective amount" refers to doses of compound sufficient to provide circulating concentrations high enough to impart a beneficial effect on the recipient thereof. The precise amount to be administered can be determined by the skilled practitioner in view of desired dosages, side effects, and medical history of the patient.

Generally, the compounds comprising Formula (I) have an $EC_{50}$ of less than about 10 nM of the binding affinity of the kappa receptor. In various embodiments, the compounds comprising Formula (I) have an $EC_{50}$ of less than about 10 nM, or less than 8 nM, or less than about 4 nM, or less than about 1 nM. I In general, the compounds of Formula (I) have an $EC_{50}$ in the Flipr Calcium assay of less than 10 nM in whole cells. In various embodiments, the compounds comprising Formula (I) have an $EC_{50}$ of less than about 10 nM, or less than 8 nM, or less than about 4 nM, or less than about 3 nM.

Definitions

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "oxygen protecting group" as used herein denotes a group capable of protecting an oxygen atom (and hence, forming a protected hydroxyl group), wherein the protecting group may be removed, subsequent to the reaction for which protection is employed, without disturbing the remainder of the molecule. Exemplary oxygen protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of oxygen protecting groups and the synthesis thereof may be found in "Greene's Protective Groups in Organic Synthesis," 4th Ed. by P. G. M. Wuts and T. W. Greene, John Wiley & Sons, Inc., 2007.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate certain embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1: Preparation of 6β-N-methylnaltrexamine (4)

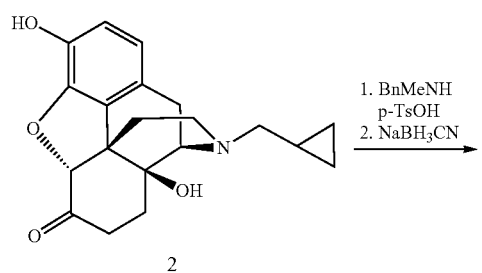

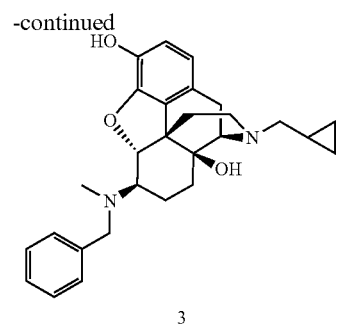

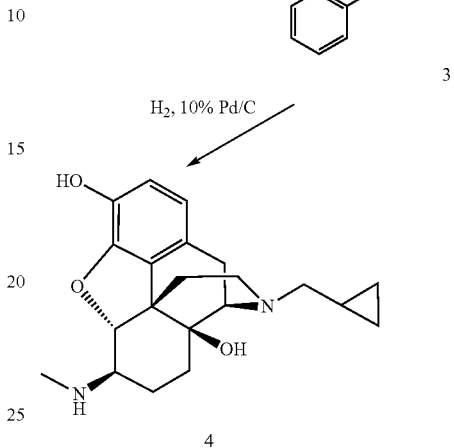

Preparation of 6β-N-benzyl-N-methylnaltrexamine (3)

To a stirred solution of naltrexone (2) (9.15 g, 26.8 mmol) in 250 ml of toluene were added N-benzylmethylamine (3.6 ml, 28 mmol) and p-toluenesulfonic acid monohydride (51 mg, 0.268 mmol). The reaction flask was equipped with a Dean-Stark trap and was refluxed for 17 hours. The toluene was removed and the crude products were dissolved in 75 ml of methanol. NaBH$_3$CN (2.1 g, 32.7 mmol) was then added to the resulting solution and the mixture was stirred at 0° C. After stirring for 2 h, LC-MS indicated the reaction was completed. The solution was concentrated on rotary evaporator. To the residue was added ethyl acetate then followed by a saturated sodium bicarbonate solution. The organic phase was separated and the aqueous phase was extracted with ethyl acetate twice. The combined organic layer was washed successively with saturated aqueous sodium bicarbonate solution, saturated aqueous NaCl solution, dried over anhydrous sodium sulfate, and then concentrated in vacuo to a residue. The residue was chromatographed on silica gel with hexane/ethyl acetate as mobile phase providing 9.2 g of compound (3) as amorphous solid.

Preparation of 6β-N-methylnaltrexamine (4)

To a Parr bottle were added 6β-N-benzyl-N-methylnaltrexamine (3) (4.3 mmol), 10% Palladium on Carbon (wetted with ca. 50% water, 190 mg), and glacial acetic acid (30 mL). The Parr bottle was attached to the Parr Hydrogenation Apparatus and flushed three times with nitrogen and then with three times with hydrogen. The mixture was reacted for 24 hours at room temperature under a pressure of 35 psi of hydrogen. A reaction aliquot was taken and LC-MS indicated the reaction was complete. The Parr bottle was removed from the Parr Hydrogenation Apparatus and the reaction mixture was filtered through celite. The filtrate was concentrated. To the residue was added water (15 mL) and the pH was then adjusted to 9 using 29% ammonia. The resulting mixture was extracted with 1:9 methanol/chloroform, the organic extracts were combined, and dried over anhydrous sodium sulfate. The dried organic solution was concentrated in vacuo, the residue was purified on silica gel column with methanol/DCM/Et$_3$N mixture as mobile phase, concentrating the collected fractions, and dried under vacuo, providing 1.2 g of product. M+H$^+$=357.47 on LC-MS; $^1$H NMR (CDCl$_3$) δ ppm 6.65 (1H, d, J=8.0 Hz), 6.54 (1H, d, J=8.0 Hz), 4.53 (1H, d, J=8.0 Hz), 3.05-2.97 (2H, m), 2.64-2.54 (3H, m), 2.49 (s, 3H), 2.36 (d, 2H, J=4 Hz), 2.22-2.13 (m, 2H), 1.95-1.92 (1H, m), 1.67-1.60 (2H, m), 1.45-1.40 (2H, m), 0.84-0.81 (1H, m), 0.52 (2H, d, J=8 Hz), 0.12-0.11 (2H, m)

Example 2: Preparation of Compounds 5(a) and 5(b)

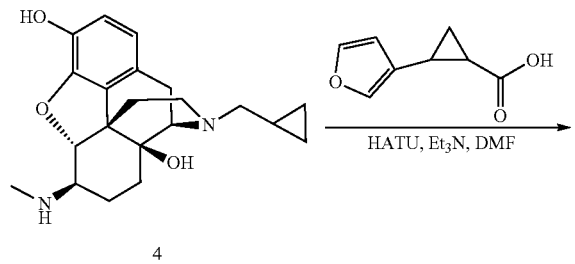

4

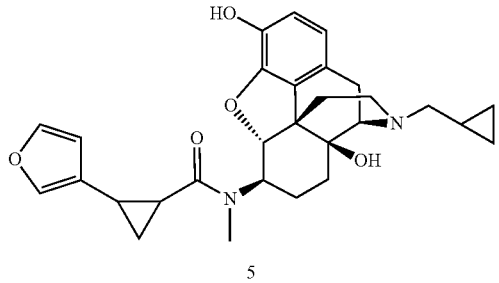

5

Preparation of 17-Cyclopropylmethyl-4,5α-epoxy-3,14β-dihydroxy-6β-((1S,2S)—N-methyl-2-(3-furyl)-cyclopropanecarboxamido)morphinan. Hydrochloride (5a)

To the mixture of 6β-N-methylnaltrexamine (4) (0.5 g, 1.4 mmol), (1S,2S)-2-(3-furyl)cyclopropane-1-carboxylic acid (0.22 g, 1.4 mmol), DMF (5.0 mL) was added HATU (1-[Bis(dimethylamino)methylene]-1H-1,2,3-triazolo[4,5-b]pyridinium 3-oxid hexafluorophosphate) (0.53 g, 1.4 mmol) and triethylamine (0.39 mL, 2.8 mmol). The resulting yellow solution was stirred at room temperature under nitrogen for two hours where LC-MS indicated the reaction was done. To the reaction solution was added ethyl acetate (70 mL). The resulting solution was washed with brine then dried over anhydrous sodium sulfate. The dried organic phase was concentrated on a rotary evaporator. The residue was purified on silica gel eluting with a mixture of Et$_3$N/MeOH/CH$_2$Cl$_2$. The collected desired fractions were concentrated under vacuum. The obtained oil product was dissolved in ethyl acetate and this solution was cooled in ice bath. To the cooled solution was added an equivalent of 1.0 N HCl in ether. The resulting mixture was concentrated under vacuum to provide 0.4 g off-white solid. M+H$^+$=491.37 on LC-MS.

Preparation of 17-Cyclopropylmethyl-4,5α-epoxy-3,14β-dihydroxy-6β-((1R,2R)—N-methyl-2-(3-furyl)-cyclopropanecarboxamido)morphinan Hydrochloride (5b)

To the mixture of 6β-N-methylnaltrexamine (4) (0.5 g, 1.4 mmol), (1R, 2R)-2-(3-furyl)cyclopropane-1-carboxylic acid (0.22 g, 1.4 mmol), DMF (5.0 mL) was added HATU (0.53 g, 1.4 mmol) and triethylamine (0.39 mL, 2.8 mmol). The resulting yellow solution was stirred at room temperature under nitrogen for two hours where LC-MS indicated the reaction was complete. To the reaction solution was added ethyl acetate (70 mL) and the resulting solution was washed with brine. The organic phase was dried over anhydrous sodium sulfate. The dried organic phase was concentrated on a rotary evaporator to a residue. The residue was purified on silica gel eluting with a mixture of Et$_3$N/MeOH/CH$_2$Cl$_2$. The collected desired fractions were concentrated under vacuum. The obtained oil product was dissolved in ethyl acetate and the resulting solution was cooled in ice bath. To this solution was added an equivalent of 1.0 N HCl in ether. The resulting mixture was concentrated under vacuum to provide 0.5 g compound (3) as off-white solid. M+H$^+$=491.36 on LC-MS.

Example 3: Preparation of 6α-N-methylnaltrexamine (6)

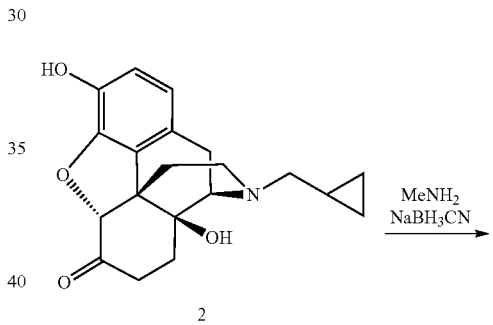

2

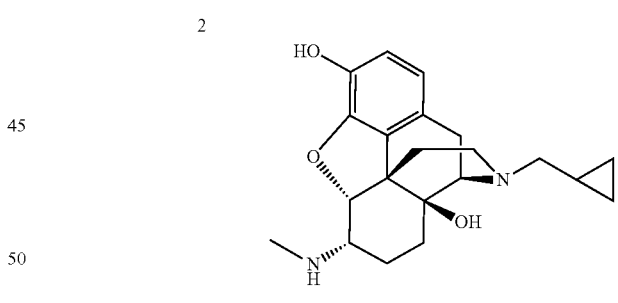

6

To the mixture of naltrexone HCl (2) (10. g, 26.5 mmol) and THF (150 mL) was added a MeNH$_2$ solution (2.0 N, 15 mL, 30 mmol). The resulting mixture was stirred at room temperature under nitrogen for 30 minutes. Then, NaHB(OAc)$_3$ (12.3 g, 56.2 mmol) was added over two hours. Then, the reaction was quenched by slowly adding 1% HCl solution (60 mL). The solution was stirred at room temperature for 15 minutes and the pH was adjusted to 8.5 with NaHCO$_3$ powder. The top organic phase was separated; the aqueous phase was extracted with MeOH/CH$_2$Cl$_2$. The combined organic extracts were dried over anhydrous sodium sulfate. The dried organic solution was concentrated under vacuum. The residue was further purified on silica gel column eluting with MeOH/CH$_2$Cl$_2$/Et$_3$N. The product was obtained as off-white solid, M+H$^+$=357.20 on LC-MS.

Example 4: Preparation of Compounds 7(a) and 7(b)

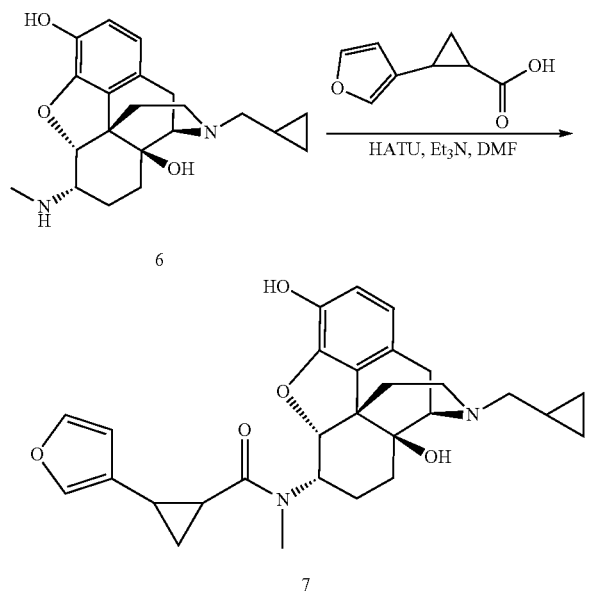

Preparation of 17-Cyclopropylmethyl-4,5α-epoxy-3,14β-dihydroxy-6α-((1S,2S)—N-methyl-2-(3-furyl)-cyclopropanecarboxamido)morphinan. Hydrochloride (7a)

To the mixture of 6α-N-methylnaltrexamine (6) (0.5 g, 1.4 mmol), (1S,2S)-2-(3-furyl)cyclopropane-1-carboxylic acid (0.22 g, 1.4 mmol), DMF (5.0 mL) was added HATU (0.53 g, 1.4 mmol) and triethylamine (0.39 mL, 2.8 mmol). The resulting yellow solution was stirred at room temperature under nitrogen for two hours where LC-MS indicated the reaction was complete. To the reaction solution was added ethyl acetate (70 mL). The resulting solution was washed with brine and the organic phase was dried over anhydrous sodium sulfate. The dried organic phase was concentrated under vacuum and the residue was purified on silica gel eluting with a mixture of Et$_3$N/MeOH/CH$_2$Cl$_2$. The collected desired fractions were concentrated under vacuum. The obtained oil product was dissolved in ethyl acetate and cooled in ice bath. To the cooled solution was added equivalent of 1.0 N HCl in ether. The resulting mixture was concentrated under vacuum to provide 0.3 g off-white solid. M+H$^+$=491.24 on LC-MS.

Preparation of 17-Cyclopropylmethyl-4,5α-epoxy-3,14β-dihydroxy-6α-((1R,2R)—N-methyl-2-(3-furyl)-cyclopropanecarboxamido)morphinan. Hydrochloride (7b)

To the mixture of 6α-N-methylnaltrexamine (6) (0.5 g, 1.4 mmol), (1R,2R)-2-(3-furyl)cyclopropane-1-carboxylic acid (0.22 g, 1.4 mmol), DMF (5.0 mL) was added HATU (0.53 g, 1.4 mmol) and triethylamine (0.39 mL, 2.8 mmol). The resulting yellow solution was stirred at room temperature under nitrogen for two hours where LC-MS indicated the reaction was complete. To the reaction solution was added ethyl acetate (70 mL). The resulting solution was washed with brine and the organic phase was dried over anhydrous sodium sulfate. The dried organic phase was concentrated on a rotary evaporator and the residue was purified on silica gel eluting with a mixture of Et$_3$N/MeOH/CH$_2$Cl$_2$. The collected desired fractions were concentrated under vacuum. The obtained oil product was dissolved in ethyl acetate and cooled in ice bath. To the cooled solution was added equivalent of 1.0 N HCl in ether. The resulting mixture was concentrated under vacuum to provide 0.35 g off-white solid. M+H$^+$=491.38 on LC-MS.

Example 5: Synthesis of 17-(1-hydroxycyclopropanemethyl)-4,5α-expoy-6β-methylamino-3,14β-dihydroxymorphinan (12)

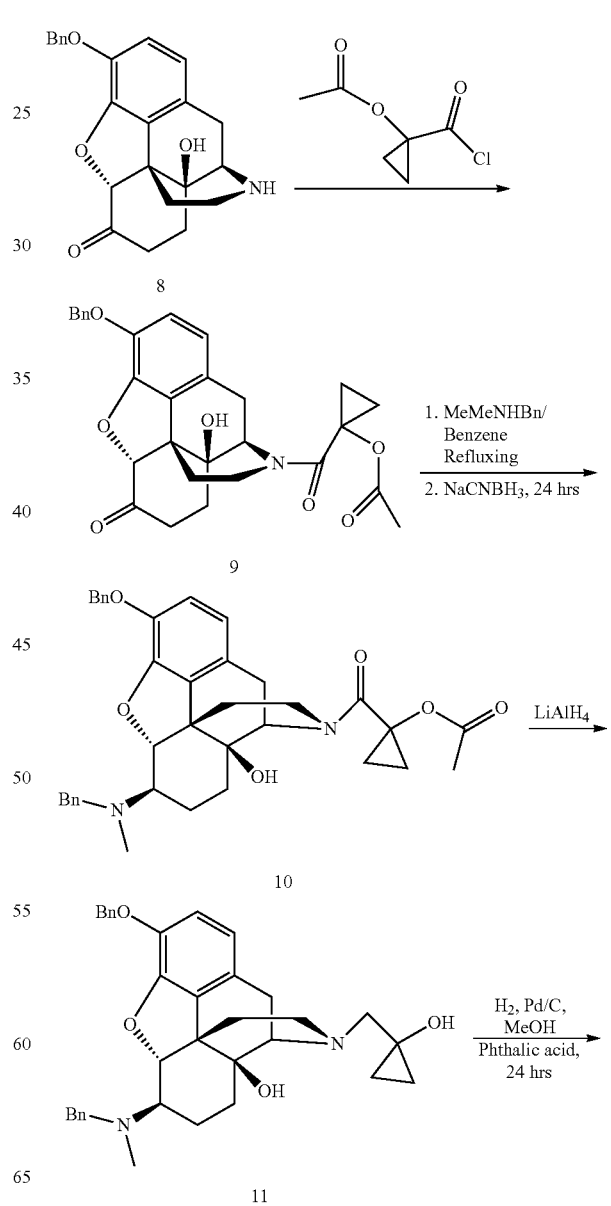

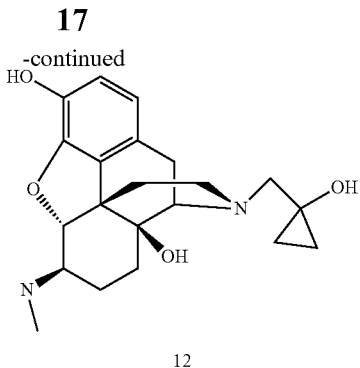

12

Synthesis of 17-(1-acetoxycyclopropanecarbox-amido)-3-benzoxy-4,5α-expoy-6-oxo-14β-hydroxymorphinan (9)

To a three-neck reaction flask under nitrogen was placed starting material (8) (14.0 g, 37.1 mmol), followed by adding dichloromethane (150 mL), and triethylamine (22.40 g, 221 mmol); the resulting mixture was cooled in ice bath, to the cold reaction was added acyl chloride (17.6 g, 122.1 mmol). After finishing addition, ice bath was removed; the reaction was stirred at room temperature for 4 hours; LC-MS analysis indicated the reaction was completed; the reaction was placed in ice bath, then water (200 mL) was added slowly to quench the reaction; the pH of the reaction mixture was adjusted to 4-5 with dilute hydrogen chloride. The organic phase was separated, the aqueous phase was extracted with dichloromethane (250 mL×3). The combined organic extracts were dried over anhydrous sodium sulfate. After filtration, the dried organic phase was concentrated under vacuum; it provided a dark yellow solid, 10.18 g, [M+H]$^+$=504.6 on LC-MS.

Synthesis of 17-(1-acetoxycyclopropanecarbox-amido)-3-benzoxy-4,5α-expoy-6β-benzyl(methyl)amino-14β-hydroxymorphinan (10)

To a three-neck reaction flask was placed the intermediate (9) (5.0 g, 9.9 mmol) and benzene (100 mL); to the resulting solution was added benzoic acid (1.21 g, 9.9 mmol) and benzylmethylamine (2.41 g, 19.8 mmol). The resulting mixture was heated to refluxing with azeotropic distillation for 24 hours. Then, the reaction was cooled to room temperature. To the reaction was added methanol (20 mL), followed by adding sodium cyano borohydride (0.94 g, 15.0 mmol). The reaction was stirred at room temperature for 2 hours. LC-MS analysis indicated the reaction was complete. To the reaction was added water (20 mL) and saturated sodium hydrogen carbonate solution (100 mL). The product was extracted with ethyl acetate (3×100 mL). The combined organic extracts were washed with brine (200 mL) and dried over anhydrous sodium sulfate. After filtration, the dried organic solution was concentrated under vacuum; the crude material was further purified on silica gel column with a mixture of ethyl acetate/hexane/methanol/triethylamine. Concentration of the collected fractions under vacuum provided an oil material, 6.0 g, [M+H]$^+$=609.7 on LC-MS.

Synthesis of 17-(1-hydroxycyclopropanemethyl)-3-benzoxy-4,5α-expoy-6β-benzyl(methyl)amino-14β-hydroxymorphinan (11)

In a three-neck reaction flask under nitrogen was placed intermediate (10) (6.0 g, 9.86 mmol) and THF. To the resulting solution was added LiAlH$_4$ (1.50 g, 39.5 mmol), the reaction was heated to reflux for 2-4 hours; LC-MS analysis indicated the reaction was completed. The reaction was cooled to room temperature, then reaction was dumped into an ice/water mixture (150 mL); to the mixture was then added 20% sodium hydroxide solution (2 mL), followed by added ethyl acetate (150 mL). The organic phase was separated and the aqueous phase was extracted with ethyl acetate (2×150 mL). The combined organic extracts were filtered through diatomaceous earth; the organic filtrate was separated and dried over anhydrous sodium sulfate. After filtration, the dried organic phase was concentrated under vacuum. The crude material was further purified on silica gel column with a mixture of ethyl acetate/hexane/methanol/triethylamine, concentration of the collected fractions under vacuum provided an oil material, 3.16 g; [M+H]$^+$=553.7 on LC-MS. $^1$H NMR (400 MHz, CDCl$_3$): 0.43-0.48 (2H, m), 0.82-0.87 (2H, m), 1.30-1.70 (4H, m), 1.95-2.8 (1H, m), 2.15-2.32 (2H, m), 2.35 (3H, s), 2.53 (1H, d, J=12.8 Hz), 2.60-2.70 (2H, m), 2.75 (1H, d, J=12.8 Hz), 2.72-2.82 (1H,m), 2.97-3.8 (2H, m), 3.72 (1H, d, J=13.6 Hz), 3.81 (1H, d, J=13.6 Hz), 4.77 (1H, d, J=7.6 Hz), 5.22 (2H, s), 6.53 (1H, d, J=8.0 Hz), 6.73 (1H, d, J=8.0 Hz), 7.15-7.51 (10H).

Synthesis of 17-(1-hydroxycyclopropanemethyl)-4,5α-expoy-6β-methylamino-3,14β-dihydroxymorphinan (12)

To the hydrogenation reaction flask was added intermediate (11) (3.16.0 g, 5.72 mmol and methanol (30 mL), followed by adding phthalic acid (1.9 g, 11.4 mmol) and 10% Pd/C (2.36 g). The reaction was carried out under hydrogen atmosphere at room temperature for 24 hours. LC-MS analysis indicated the reaction was complete. The reaction was filtered through diatomaceous earth and the filtrate was concentrated under vacuum to provide a grey solid, 3.38 g. [M+H]$^+$=373.5 on LC-MS.

Example 6: Preparation of 17-(1-hydroxycyclopropanemethyl)-4,5α-expoy-6α-methylamino-3,14β-dihydroxymorphinan (15)

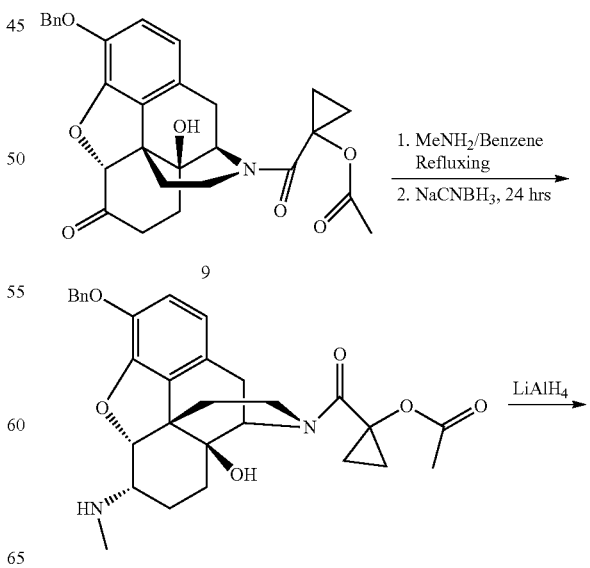

-continued

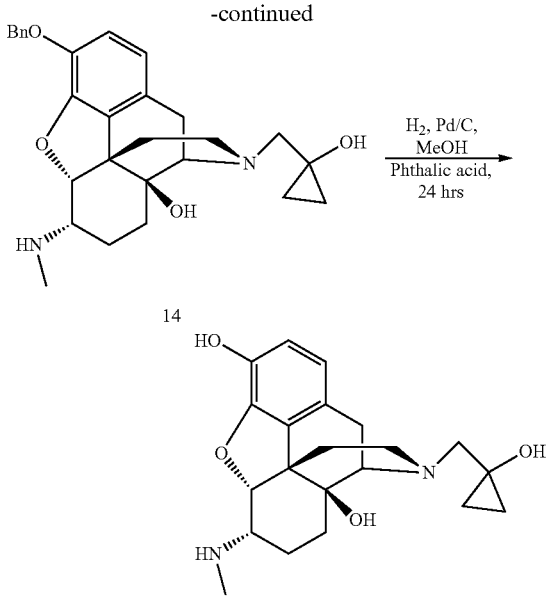

Synthesis of 17-(1-acetoxycyclopropanecarbox-amido)-3-benzoxy-4,5α-expoy-6α-benzyl(methyl) amino-14β-hydroxymorphinan (13)

To a three-neck round bottom flask were added intermediate (9) (3.0 g, 5.96 mmol) and methanol (10 mL), followed by adding 30% methylamine in methanol (2.4 g, 23.1 mmol), and acetic acid (0.1 mL). The resulting mixture was stirred at room temperature for 2 hours and then the reaction was placed in ice bath. Sodium cyanoborohydride (1.5 g, 23.9 mmol) was added. The ice bath was removed and the reaction was stirred at room temperature for 24 hours. LC-MS analysis indicated the reaction was complete. To the reaction was added water (50 mL) and followed by adding ethyl acetate (150 mL). The mixture's pH was adjusted to ~8 with saturated sodium bicarbonate solution. The organic phase was separated and the aqueous phase was extracted with ethyl acetate (150 mL×2). The combined organic extracts were dried over anhydrous sodium sulfate. Concentrating the dried organic extracts under vacuum provided a solid, 3.15 g. $[M+H]^+$=519.6 on LC-MS.

Synthesis of 17-(1-hydroxycyclopropanemethyl)-3-benzoxy-4,5α-expoy-6α-methylamino-14β-hydroxymorphinan (14)

In a three-neck reaction flask under nitrogen was placed intermediate (13) (3.15 g, 6.07 mmol) and THF (30 mL). To the resulting solution was added LiAlH₄ ((0.69 g, 18.2 mmol); the reaction was heated to reflux for 2-4 hours; LC-MS analysis indicated the reaction was completed. The reaction was cooled to room temperature and then poured into an ice/water mixture (100 mL). To the mixture was then added 20% sodium hydroxide solution (1.5 mL) followed by added ethyl acetate (100 mL). The organic phase was separated and the aqueous phase was extracted with ethyl acetate (2×100 mL). The combined organic extracts were filtered through diatomaceous earth, the organic filtrate was separated, and dried over anhydrous sodium sulfate. After filtration, the dried organic phase was concentrated under vacuum to provide an oil. 1.98 g; $[M+H]^+$=463.6 on LC-MS.

Synthesis of 17-(1-hydroxycyclopropanemethyl)-4,5α-expoy-6α-methylamino-3,14β-dihydroxymorphinan (15)

To the hydrogenation reaction flask under nitrogen was placed intermediate (14) (3.16.0 g, 5.72 mmol) and methanol (30 mL), followed by adding phthalic acid (1.42 g, 8.54 mmol) and 10% Pd/C (1.78 g). The reaction was then carried out under hydrogen atmosphere at room temperature for 24 hours. LC-MS analysis indicated the reaction was complete. The reaction was filtered through diatomaceous earth and was concentrated under vacuum to provide a grey solid, 2.72 g. $[M+H]^+$=373.5 on LC-MS.

Example 7: Preparation of Compounds 16(a) and 16(b)

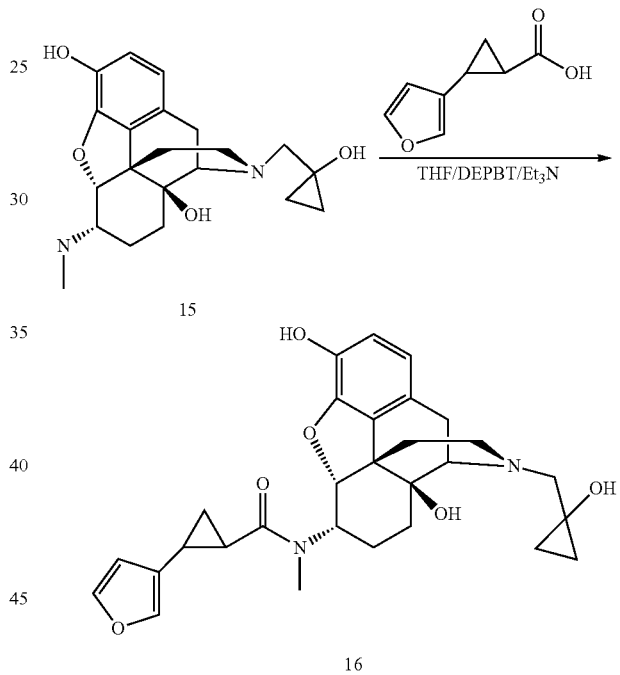

Preparation of 17-(1-hydroxylcyclopropylmethyl-4,5α-epoxy-3,14β-dihydroxy-6α-((1S,2S)—N-methyl-2-(3-furyl)-cyclopropanecarboxamido)morphinan trifluoroacetate (16a)

To the three-neck reaction flask under nitrogen at room temperature were added (1S,2S)-2-(3-furyl)cyclopropane-1-carboxylic acid (20 mg, 0.134 mmol), intermediate (15) (50 mg, 0.134 mmol) and THF (1.0 mL); after the solid was dissolved under stirring, DEPBT (3-(diethoxyphosphoryloxy)-1,2,3-benzotriazin-4(3H)-one) (80 mg, 0.268 mmol) and triethylamine (27 mg, 0.268 mmol) were added. The reaction was stirred at room temperature overnight. LC-MS analysis indicated the reaction was complete. The solvent was removed under vacuum. To the residue was added dichloromethane (2.0 mL). The resulting solution was washed with 5% NaHSO₄ aqueous solution (2.0 mL×3), 5% aqueous NaHCO₃ solution (2.0 mL×3), and brine (2.0 mL×3). The organic phase was dried over anhydrous sodium sulfate and filtered. The filtrate was then concentrated under vacuum. The residue was further purified on reverse phase LC with mobile phase (A: 0.01% TFA/H₂O, B: 100% ACN). The collected fractions were combined and the product was obtained as white powder after lyophilization, 10 mg, yield=14.7%. [M+H]⁺=507.6 on LC-MS.

Preparation of 17-(1-hydroxylcyclopropylmethyl-4, 5α-epoxy-3,14β-dihydroxy-6α-((1R,2R)—N-methyl-2-(3-furyl)-cyclopropanecarboxamido)morphinan. trifluoroacetate (16b)

To the three-neck reaction flask under nitrogen at room temperature were added (1R,2R)-2-(3-furyl)cyclopropane-1-carboxylic acid (20 mg, 0.134 mmol), intermediate (15) (50 mg, 0.134 mmol) and THF (1.0 mL); after the solid was dissolved under stirring, DEPBT (80 mg, 0.268 mmol) and triethylamine (27 mg, 0.268 mmol) were added. The reaction was stirred at room temperature overnight. LC-MS analysis indicated the reaction was complete and the solvent was removed under vacuum. To the residue was added dichloromethane (2.0 mL). The resulting solution was washed with 5% aqueous NaHSO₄ solution (2.0 mL×3), 5% aqueous NaHCO₃ solution (2.0 m×3 L), and brine (2.0 mL×3). The organic phase was dried over anhydrous sodium sulfate and filtered. The filtrate was then concentrated under vacuum, the residue was further purified on preparation LC with mobile phase (A: 0.01% TFA/H2O, B: 100% ACN). The collected fractions were combined; the product was obtained as white powder after lyophilization: 14 mg, yield=20.6%. M+H⁺=507.6 on LC-MS.

Example 8: Preparation of Compounds 17(a) and 17(b)

Preparation of 17-(1-hydroxylcyclopropylmethyl)-4, 5α-epoxy-3,14β-dihydroxy-6β-((1S,2S)—N-methyl-2-(3-furyl)-cyclopropanecarboxamido)morphinan. trifluoroacetate (17a)

To the three-neck reaction flask under nitrogen at room temperature was added (1S,2S)-2-(3-furyl)cyclopropane-1-carboxylic acid (20 mg, 0.134 mmol), intermediate (12) (50 mg, 0.134 mmol) and THF (1.0 mL); after the solid was dissolved under stirring, DEPBT (80 mg, 0.268 mmol) and triethylamine (27 mg, 0.268 mmol) were added. The reaction was stirred at room temperature overnight. LC-MS analysis indicated the reaction was complete. The solvent was removed under vacuum. To the residue was added dichloromethane (2.0 mL), the resulting solution was washed with 5% aqueous NaHSO₄ solution (2.0 mL×3), 5% aqueous NaHCO₃ solution (2.0 mL×3), and brine (2.0 mL×3). The organic phase was dried over anhydrous sodium sulfate. The filtrate was then concentrated under vacuum and the residue was further purified on preparation LC with mobile phase (A: 0.01% TFA/H2O, B: 100% AC). The collected fractions were combined; the product was obtained as white powder after lyophilization, 14 mg, yield=20.6%. [M+H]⁺=507.6 on LC-MS.

Preparation of 17-(1-hydroxylcyclopropylmethyl-4, 5α-epoxy-3,14β-dihydroxy-6β-((1R,2R)—N-methyl-2-(3-furyl)-cyclopropanecarboxamido)morphinan. trifluoroacetate (17b)

To the three-neck reaction flask under nitrogen at room temperature were added (1R,2R)-2-(3-furyl)cyclopropane-1-carboxylic acid (20 mg, 0.134 mmol), intermediate (12) (50 mg, 0.134 mmol) and THF (1.0 mL); after the solid was dissolved under stirring, DEPBT (80 mg, 0.268 mmol) and triethylamine (27 mg, 0.268 mmol) were added. The reaction was stirred at room temperature overnight. LC-MS analysis indicated the reaction was complete. The solvent was removed under vacuum. To the residue was added dichloromethane (2.0 mL), the resulting solution was washed with 5% aqueous NaHSO₄ solution (2.0 mL×3), 5% aqueous NaHCO₃ solution (2.0 mL×3), and brine (2.0 mL×3). The organic phase was dried over anhydrous sodium sulfate and filtered. The filtrate was then concentrated under vacuum and the residue was further purified on preparation LC with mobile phase (A: 0.01% TFA/H₂O, B: 100% ACN). The collected fractions were combined; the product was obtained as white powder after lyophilization yielding a white powder, 21 mg, yield=30.9%. [M+H]⁺=507.6 on LC-MS.

Example 9: Preparation of Compounds 18(a) and 18(b)

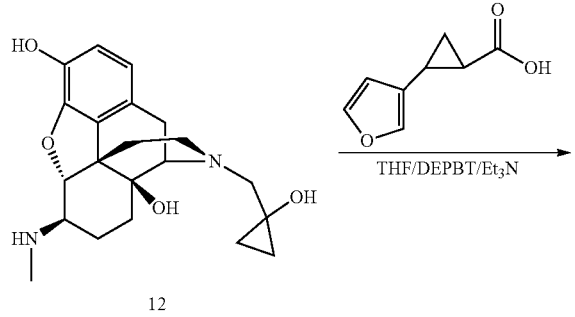

12

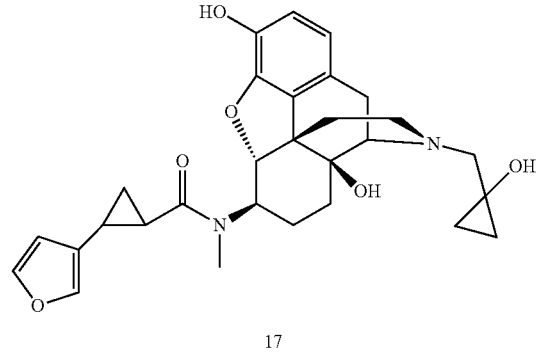

17

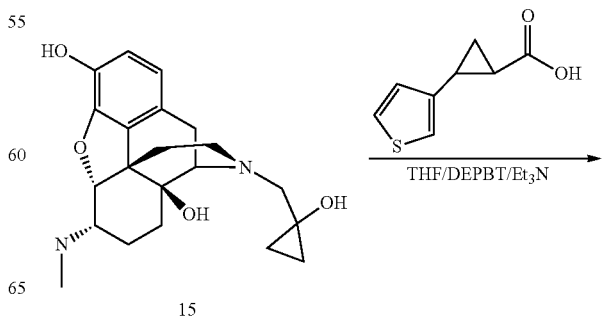

15

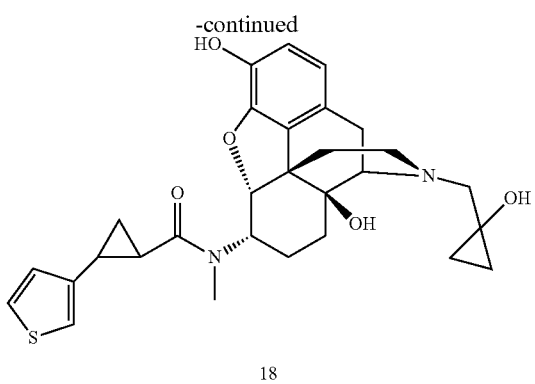

18

Preparation of 17-(1-hydroxylcyclopropylmethyl-4, 5α-epoxy-3,14β-dihydroxy-6α-((1S,2S)—N-methyl-2-(3-thienyl)-cyclopropanecarboxamido)morphinan. trifluoroacetate (18a)

To the three-neck reaction flask under nitrogen at room temperature were added (1S,2S)-2-(3-thienyl)cyclopropane-1-carboxylic acid (22.5 mg, 0.134 mmol), intermediate (15) (50 mg, 0.134 mmol) and THF (1.0 mL); after the solid was dissolved under stirring, DEPBT (80 mg, 0.268 mmol) and triethylamine (27 mg, 0.268 mmol) were added. The reaction was stirred at room temperature overnight. LC-MS analysis indicated the reaction was complete and the solvent was removed under vacuum. To the residue was added dichloromethane (2.0 mL) and the resulting solution was washed with 5% aqueous NaHSO$_4$ solution (2.0 mL), 5% aqueous NaHCO$_3$ solution (2.0 mL), and brine (2.0 mL×3). The organic phase was dried over anhydrous sodium sulfate and filtered. The filtrate was then evaporated under vacuum and the residue was further purified on preparation LC with mobile phase (A: 0.01% TFA/H$_2$O, B: 100% ACN). The collected fractions were combined; the product was obtained as white powder after lyophilization, 15 mg, yield=21.4%. [M+H]$^+$=523.7 on LC-MS.

Preparation of 17-(1-hydroxylcyclopropylmethyl-4, 5α-epoxy-3,14β-dihydroxy-6α-((1R,2R)—N-methyl-2-(3-thienyl)-cyclopropanecarboxamido) morphinan. trifluoroacetate (18b)

To the three-neck reaction flask under nitrogen at room temperature were added (1R,2R)-2-(3-thienyl)cyclopropane-1-carboxylic acid (22.5 mg, 0.134 mmol), intermediate (15) (50 mg, 0.134 mmol) and THF (1.0 mL); after the solid was dissolved under stirring, DEPBT (80 mg, 0.268 mmol) and triethylamine (27 mg, 0.268 mmol) were added. The reaction was stirred at room temperature overnight. LC-MS analysis indicated the reaction was done. The solvent was removed under vacuum. To the residue was added dichloromethane (2.0 mL), the resulting solution was washed with 5% aqueous NaHSO$_4$ solution (2.0 mL), 5% aqueous NaHCO$_3$ solution (2.0 mL), and brine (2.0 mL×3). The organic phase was dried over anhydrous sodium sulfate and filtered. The filtered organic phase was then evaporated under vacuum. The residue was further purified on preparation LC with mobile phase (A: 0.01% TFA/H$_2$O, B: 100% ACN). The collected fractions were combined; the product was obtained as white powder after lyophilization, 6.5 mg, yield=9.3%. [M+H]$^+$=523.7 on LC-MS.

Example 10: Preparation of Compounds 19(a) and 19(b)

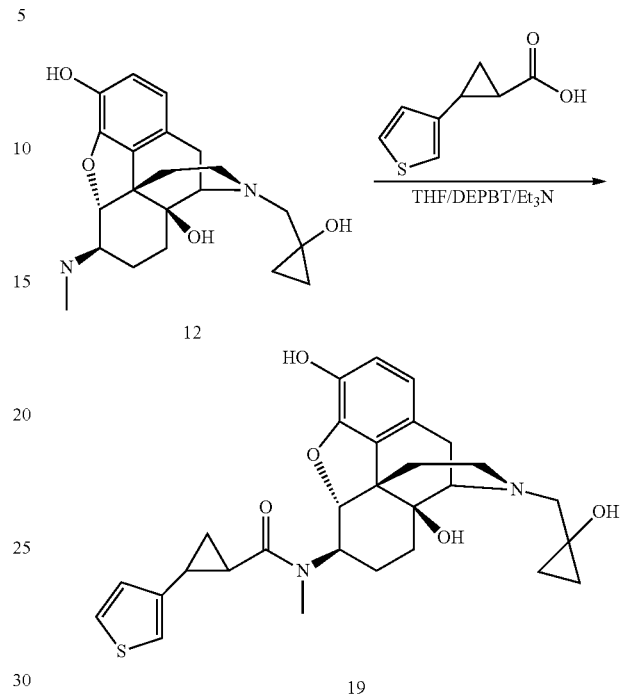

Preparation of 17-(1-hydroxylcyclopropylmethyl-4, 5α-epoxy-3,14β-dihydroxy-6β-((1S,2S)—N-methyl-2-(3-thienyl)-cyclopropanecarboxamido)morphinan. trifluoroacetate (19a)

To the three-neck reaction flask under nitrogen at room temperature were added (1S,2S)-2-(3-thienyl)cyclopropane-1-carboxylic acid (22.5 mg, 0.134 mmol), intermediate 12 (50 mg, 0.134 mmol) and THF (1.0 mL); after the solid was dissolved under stirring, DEPBT (80 mg, 0.268 mmol) and triethylamine (27 mg, 0.268 mmol) were added. The reaction was stirred at room temperature overnight. LC-MS analysis indicated the reaction was complete. The solvent was removed under vacuum. To the residue was added dichloromethane (2.0 mL). The resulting solution was washed with 5% aqueous NaHSO$_4$ solution (2.0 mL), 5% aqueous NaHCO$_3$ solution (2.0 mL), and brine (2.0 mL×3). The organic phase was dried over anhydrous sodium sulfate and filtered. The filtrate was then concentrated under vacuum. The residue was further purified on reverse phase LC with mobile phase (A: 0.01% TFA/H$_2$O, B:100% ACN). The collected fractions were combined; the product was obtained as white powder after lyophilization, 13 mg, yield=18.5%. [M+H]$^+$=523.7 on LC-MS.

Preparation of 17-(1-hydroxylcyclopropylmethyl-4, 5α-epoxy-3,14β-dihydroxy-6β-((1R,2R)—N-methyl-2-(3-thienyl)-cyclopropanecarboxamido) morphinan. trifluoroacetate (19b)

To the three-neck reaction flask under nitrogen at room temperature were added (1R,2R)-2-(3-thienyl)cyclopropane-1-carboxylic acid (22.5 mg, 0.134 mmol), intermediate 12 (50 mg, 0.134 mmol) and THF (1.0 mL); after the solid was dissolved under stirring, DEPBT (80 mg, 0.268 mmol) and triethylamine (27 mg, 0.268 mmol) were added. The reaction was stirred at room temperature overnight. LC-MS analysis indicated the reaction was complete. The solvent was removed under vacuum. To the residue was added dichloromethane (2.0 mL), the resulting solution was washed with 5% aqueous NaHSO₄ solution (2.0 mL×3), 5% aqueous NaHCO₃ solution (2.0 mL×3), and brine (2.0 mL×3). The organic phase was dried over anhydrous sodium sulfate and filtered. The filtrate was then evaporated under vacuum. The residue was further purified on preparation LC with mobile phase (A: 0.01% TFA/H₂O, B: 100% ACN). The collected fractions were combined; the product was obtained as white powder after lyophilization, 14 mg, yield=20.0%. [M+H]⁺=523.7 on LC-MS.

Example 11: Preparation of Compounds 20(a) and 20(b)

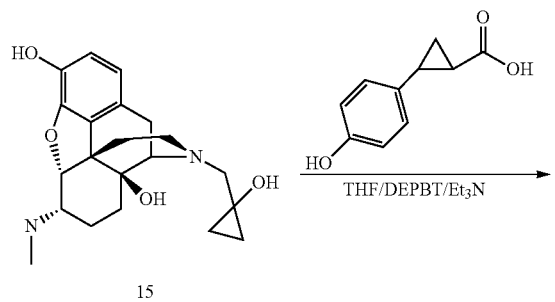

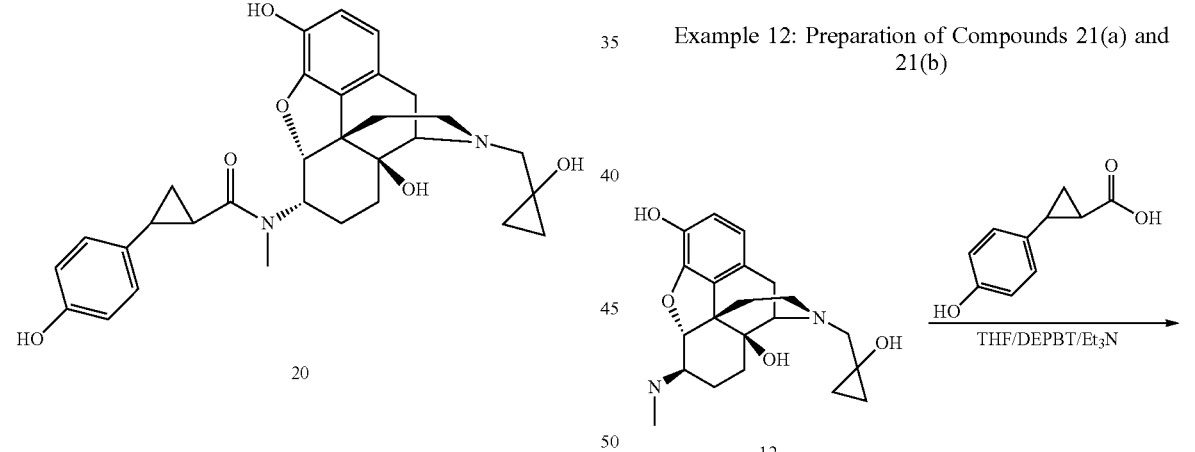

Preparation of 17-(1-hydroxylcyclopropylmethyl-4,
5α-epoxy-3,14β-dihydroxy-6α-((1S,2S)—N-methyl-
2-(3-(4-hydroxylphenyl)-cyclopropanecarboxamido)
morphinan. trifluoroacetate (20a)

To the three-neck reaction flask under nitrogen at room temperature were added (1S,2S)-2-(3-thienyl)cyclopropane-1-carboxylic acid (23.9 mg, 0.134 mmol), intermediate (15) (50 mg, 0.134 mmol) and THF (1.0 mL); after the solid was dissolved under stirring, DEPBT (80 mg, 0.268 mmol) and triethylamine (27 mg, 0.268 mmol) were added. The reaction was stirred at room temperature overnight. LC-MS analysis indicated the reaction was complete. The solvent was removed under vacuum. To the residue was added dichloromethane (2.0 mL), the resulting solution was washed with 5% aqueous NaHSO₄ solution (2.0 mL), 5% aqueous NaHCO₃ solution (2.0 mL), and brine (2.0 mL×3). The organic phase was dried over anhydrous sodium sulfate and filtered. The filtrate was then concentrated under vacuum and the obtained residue was further purified on preparation LC with mobile phase (A: 0.01% TFA/H₂O, B:100% ACN). The collected fractions were combined; the product was obtained as white powder after lyophilization, 16 mg, yield=22.4%. [M+H]⁺=533.6 on LC-MS.

Preparation of 17-(1-hydroxylcyclopropylmethyl-4,
5α-epoxy-3,14β-dihydroxy-6α-((1R,2R)—N-methyl-2-(3-(4-hydroxylphenyl)-cyclopropanecarboxamido)morphinan trifluoroacetate (20b)

To the three-neck reaction flask under nitrogen at room temperature were added (1R,2R)-2-(3-(4-hydroxylphenyl) cyclopropane-1-carboxylic acid (23.9 mg, 0.134 mmol), intermediate (15) (50 mg, 0.134 mmol) and THF (1.0 mL); after the solid was dissolved under stirring, DEPBT (80 mg, 0.268 mmol) and triethylamine (27 mg, 0.268 mmol) were added. The reaction was stirred at room temperature overnight. LC-MS analysis indicated the reaction was complete. The solvent was removed under vacuum. To the residue was added dichloromethane (2.0 mL), the resulting solution was washed with 5% aqueous NaHSO₄ solution (2.0 mL×2), 5% aqueous NaHCO₃ solution (2.0 mL×2), and brine (2.0 mL×3). The organic phase was dried over anhydrous sodium sulfate and filtered. The filtrate was then concentrated under vacuum. The residue was further purified on reverse phase LC with mobile phase (A: 0.01% TFA/H₂O, B: 100% ACN). The collected fractions were combined; the product was obtained as white powder after lyophilization, 13 mg, yield=18.2%. [M+H]⁺=533.6 on LC-MS.

Example 12: Preparation of Compounds 21(a) and 21(b)

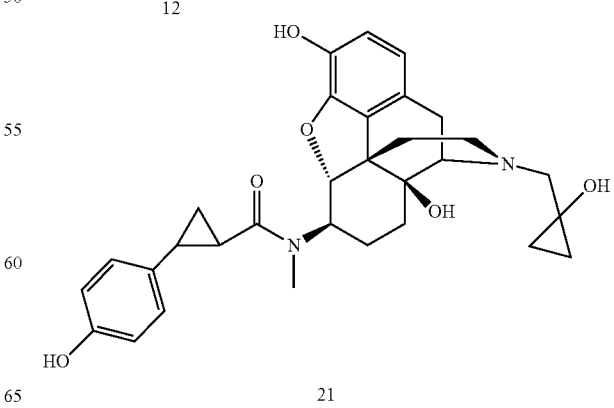

Preparation of 17-(1-hydroxylcyclopropylmethyl-4, 5α-epoxy-3,14β-dihydroxy-6β-((1S,2S)—N-methyl-2-(3-(4-hydroxylphenyl)-cyclopropanecarboxamido) morphinan trifluoroacetate (21a)

To the three-neck reaction flask under nitrogen at room temperature were added (1S,2S)-2-(3-(4-hydroxylphenyl) cyclopropane-1-carboxylic acid (23.9 mg, 0.134 mmol), intermediate (12) (50 mg, 0.134 mmol) and THF (1.0 mL); after the solid was dissolved under stirring, DEPBT (80 mg, 0.268 mmol) and triethylamine (27 mg, 0.268 mmol) were added. The reaction was stirred at room temperature overnight. LC-MS analysis indicated the reaction was complete. The solvent was removed under vacuum. To the residue was added dichloromethane (2.0 mL), the resulting solution was washed with 5% aqueous NaHSO$_4$ solution (2.0 mL), 5% aqueous NaHCO$_3$ aqueous solution (2.0 mL), and brine (2.0 mL×3). The organic phase was dried over anhydrous sodium sulfate and filtered. The filtrate was then evaporated under vacuum, the residue was further purified on preparation LC with mobile phase (A: 0.01% TFA/H$_2$O, B: 100% ACN). The collected fractions were combined; the product was obtained as white powder after lyophilization, 11 mg, yield=15.4%. [M+H]$^+$=533.6 on LC-MS.

Preparation of 17-(1-hydroxylcyclopropylmethyl-4, 5α-epoxy-3,14β-dihydroxy-6β-((1R,2R)—N-methyl-2-(3-(4-hydroxylphenyl)-cyclopropanecarboxamido)morphinan trifluoroacetate (21b)

To the three-neck reaction flask under nitrogen at room temperature was added (1R,2R)-2-(3-(4-hydroxylphenyl) cyclopropane-1-carboxylic acid (23.9 mg, 0.134 mmol), intermediate (12) (50 mg, 0.134 mmol) and THF (1.0 mL); after the solids were dissolved under stirring, DEPBT (80 mg, 0.268 mmol) and triethylamine (27 mg, 0.268 mmol) were added. The reaction was stirred at room temperature overnight. LC-MS analysis indicated the reaction was complete. The solvent was removed under vacuum. To the residue was added dichloromethane (2.0 mL), the resulting solution was washed with 5% aqueous NaHSO$_4$ solution (2.0 mL×3), 5% aqueous NaHCO$_3$ solution (2.0 mL×3), and brine (2.0 mL×3). The organic phase was dried over anhydrous sodium sulfate and filtered. The filtrate was then evaporated under vacuum. The residue was further purified on preparation LC with mobile phase (A: 0.01% TFA/H$_2$O, B: 100% ACN). The collected fractions were combined; the product was obtained as white powder after lyophilization, 10 mg, yield=14.0%. [M+H]$^+$=533.6 on LC-MS.

Example 13: Preparation of Compounds 23(a) and 23(b)

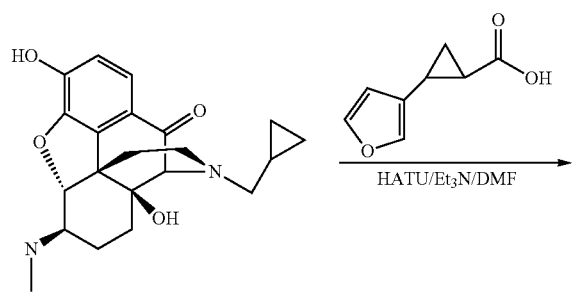

22

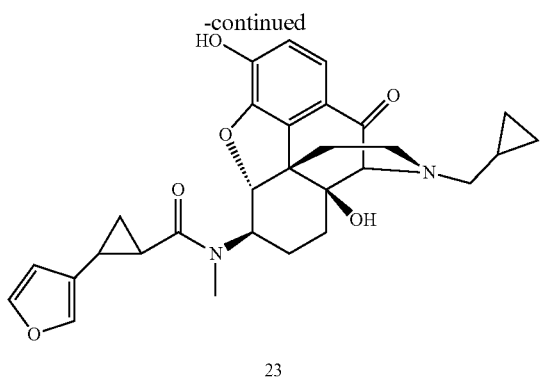

23

Preparation of 17-cyclopropylmethyl-10-oxo-4,5α-epoxy-3,14β-dihydroxy-6β-((1S,2S)—N-methyl-2-(3-(4-hydroxylphenyl)-cyclopropanecarboxamido) morphinan. hydrochloride (23a)

To the mixture of intermediate (22) (prepared based on literature method (Chem. Pharm. Bull. 2004, 52(6), 664-669) (0.5 g, 1.4 mmol), (1S,2S)-2-(3-furyl)cyclopropane-1-carboxylic acid (0.22 g, 1.4 mmol), DMF (5.0 mL) was added HATU (1-[bis(dimethylamino)methylene]-1H-1,2,3-triazolo[4,5-b]pyridinium 3-oxid hexafluorophosphate) (0.53 g, 1.4 mmol) and triethylamine (0.39 mL, 2.8 mmol). The resulting yellow solution was stirred at room temperature under nitrogen until LC-MS analysis indicated the reaction was complete. To the reaction solution was added ethyl acetate (70 mL). The resulting solution was washed with brine, dried over anhydrous sodium sulfate, and then filtered. The dried organic phase was concentrated under vacuum. The residue was purified on silica gel eluting with a mixture of Et$_3$N/MeOH/CH$_2$Cl$_2$. The collected desired fractions were concentrated under vacuum. The obtained oil product was dissolved in ethyl acetate and this solution was cooled in ice bath. To the cooled solution was added an equivalent of 1.0 N HCl in ether. The resulting mixture was concentrated under vacuum to provide 0.14 g off-white solid. [M+H]$^+$=505.37 on LC-MS.

Preparation of 17-cyclopropylmethyl-10-oxo-4,5α-epoxy-3,14β-dihydroxy-6β-((1R,2R)—N-methyl-2-(3-(4-hydroxylphenyl)-cyclopropanecarboxamido) morphinan hydrochloride (23b)

To the mixture of intermediate (22) (prepared based on literature method (Chem. Pharm. Bull. 2004, 52(6) 664-669) (0.5 g, 1.4 mmol), (1R,2R)-2-(3-furyl)cyclopropane-1-carboxylic acid (0.22 g, 1.4 mmol), DMF (5.0 mL) was added HATU (1-[bis(dimethylamino)methylene]-1H-1,2,3-triazolo[4,5-b]pyridinium 3-oxid hexafluorophosphate) (0.53 g, 1.4 mmol) and triethylamine (0.39 mL, 2.8 mmol). The resulting yellow solution was stirred at room temperature under nitrogen until LC-MS analysis indicated the reaction was complete. To the reaction solution was added ethyl acetate (70 mL). The resulting solution was washed with brine, dried over anhydrous sodium sulfate, and then filtered. The dried organic phase was concentrated under vacuum. The residue was purified on silica gel eluting with a mixture of Et$_3$N/MeOH/CH$_2$Cl$_2$. The collected desired fractions were concentrated under vacuum. The obtained oil product was dissolved in ethyl acetate and this solution was cooled in ice bath. To the cooled solution was added an equivalent of 1.0 N HCl in ether. The resulting mixture was concentrated under vacuum to provide 0.25 g off-white solid. [M+H]$^+$=505.38 on LC-MS.

Example 14: Opioid Receptor Binding Assay

The measurement of opioid receptor binding affinity was conducted using a radioligand binding assay on the membranes prepared from HEK293 cells (human embryonic kidney cell line) that were heterologously expressed for the recombinant human mu, delta or kappa opioid receptors.

The assay buffers used for opioid receptor binding studies were 50 mM Tris.HCl (pH 7.4) for KOR, 50 mM Tris.HCl (pH 7.4) with 5 mM MgCl$_2$ for MOR, and 50 mM Tris.HCl (pH 7.4) with 10 mM MgCl$_2$ plus 1 mM EDTA for DOR. Wash buffer was containing 50 mM Tris.HCl with pH 7.4.

The opioid receptor binding affinity were compared to three known standards: Naltrindole, U-50488 (trans-(+)-3, 4-dichloro-N-methyl-N-[2-(1-pyrrolidinyl)cyclohexyl]phenylacetamide, see M. Doi, T. Ishida and M, Inoue; Structure of K-agonist, U-50488 Acta Cryst. (1990). C46, 676-678), and DAMGO (D-Ala2 MePhe4, Gly(ol)5]encephalin, see Allan D. Blake, George Bot, John C. Freeman, and Terry Reisine‡ Differential Opioid Agonist Regulation of the Mouse m Opioid Receptor* THE JOURNAL OF BIOLOGICAL CHEMISTRY Vol. 272, No. 2, Issue of January 10, pp. 782-790, 1997).

The radio ligands were prepared at the final concentration of 0.5 nM for [$^3$H]DAMGO, 0.5 nM for [$^3$H]diprenorphine, and 0.5 nM for [$^3$H] DADLE, which were used as the competing radioligands for mu, kappa and delta receptor respectively.

Cell membrane of HEK293 cells transfected with opioid receptors was prepared in the amount of 20 ug of MOR, 6.7 ug of KOR and 6.7 ug of DOR per each well respectively. These membranes containing the receptor of interest were incubated with increasing concentrations of test compound in the presence of a single concentration of radioligand. The fixed concentration of the radioligand was used and serial dilutions of the test compound were prepared.

Testing started at 10 uM of testing compound to 4-fold serial dilution for 8-points detection. Transfer 1 µl of compounds/high control/low control to the 96 well plates according to the plate map, then dispense 100 µl of membrane stock solution into the plate, add 100 µl of radio ligand solution. Incubation was carried out for 1 hour at room temperature with 300 rpm gentle agitation. Then, soaked the Unifilter-96 GF/C filter plates with 50 µl of 0.3% Poly ethyleneimine per well for at least 0.5 hour at room temperature, and filtered the reaction mixture through the plates using FilterMate™ harvester, then wash each plate for four times with cold wash buffer. The filter plates are then dried for 1 hour at 50° C. After drying, the filter was sealed in polyethylene and adds 50 µl of Perkin Elmer Microscint 20 cocktail and the radioactivity counted in a Perkin Elmer MicroBeta2 counter.

Specific binding is determined by subtraction of the Bound CPM values in the presence of 50-100× excess of cold ligand. Data is fitted using the saturation analysis non-linear curve fitting routines in Prism®. Calculate the inhibition using following equation:

% Inhibition=(1−(Assay well−Average_LC)/(Average_HC−Average_LC))*100%

Binding data are analyzed using GraphPad Prism 5.0 and IC$_{50}$ is generated by non-linear regression from dose response curves. Use the model "log (inhibitor) vs. response—Variable slope" to fit the data. This data is shown in Table 1.

TABLE 1

| | | Binding Affinity | | | Selectivity | |
| | | Kappa IC$_{50}$ | Mu IC$_{50}$ | Delta IC$_{50}$ | | |
| # | Compounds | (nM) | (nM) | (nM) | µ/k | δ/k |
|---|---|---|---|---|---|---|
| 1 | U-50488 | 14.59 | — | — | — | — |
| 2 | DAMGO | — | 0.68 | — | — | — |
| 3 | Naltrindole | — | — | 0.18 | — | — |
| 4 | 5a | 0.42 | 10.73 | 86.46 | 1.76 | 207.59 |
| 5 | 5b | 7.76 | 3.47 | 69.01 | 0.45 | 8.90 |
| 6 | 7a | 0.05 | 0.3 | 0.66 | 5.85 | 12.6 |
| 7 | 7b | 0.24 | 0.52 | 0.68 | 2.16 | 2.82 |
| 8 | 16a | 0.94 | 1.55 | 5.46 | 1.65 | 5.80 |
| 9 | 16b | 6.74 | 7.18 | 34.05 | 1.07 | 5.05 |
| 10 | 17a | 1.22 | 4.96 | 43.07 | 4.07 | 35.3 |
| 11 | 17b | 6.49 | 45.37 | 71.58 | 6.99 | 11.0 |
| 12 | 18a | 0.97 | 1.58 | 10.93 | 1.63 | 11.3 |
| 13 | 18b | 6.15 | 76.83 | 118.0 | 12.5 | 19.2 |
| 14 | 19a | 0.17 | 1.37 | 16.34 | 8.05 | 96.1 |
| 15 | 19b | 0.46 | 5.98 | 146.8 | 13.0 | 319 |
| 16 | 20a | 102.3 | 119.3 | 160.9 | 1.12 | 1.57 |
| 17 | 20b | 16.02 | 8.08 | 11.76 | 0.50 | 0.73 |
| 18 | 21a | 0.85 | 1.25 | 30.23 | 1.47 | 35.6 |
| 19 | 21b | >200 | 114.2 | 385 | <0.57 | <1.93 |
| 20 | 23a | 0.070 | 12.2 | 261.2 | 174.3 | 3731 |
| 21 | 23b | 0.62 | 73.71 | 528.2 | 118.9 | 1331 |

As the data in the above table indicated, the compounds 5a, 5b, 7a, 7b, 18a, 19a, and 21a provided better IC$_{50}$ then U-50488.

Example 15: FLIPR Calcium Assay in Whole Cells

The FLIPR Calcium Assay is used to measure the ability of an opioid ligand to induce a functional response upon receptor binding.

The MOR, DOR and KOR are G-protein coupled receptors (GPCRs) which play an important role in cell signaling. The receptor is activated by a ligand then triggering G-protein activation inside the cell. An activated G-protein induces various cascades of intracellular messengers including calcium flux. The functional cell-based assays evaluated the changes of intracellular calcium level which were detected through use of fluorescent calcium-sensitive reporter dyes. The basic system of performing a calcium mobilization assay includes the FLIPR Calcium Assay Kit and the FLIPR Tetra® System, which were used to observe changes in intracellular calcium levels and determine the dose-response in HEK293 cells transfected with the recombinant human mu, delta or kappa opioid receptors.

The cells used in the assay were grown in the culture medium of 88% DMEM which contains 10% FBS, 300 ug/mL G418, 2 ug/mL Blasticidin, 1% GlutaMax and 1% Penicillin/Streptomycin (Hyclone-SV30010). Seeded 20000 cells in 20 uL medium to each well of assay plate (Greiner-781946), and the cells were maintained at 37° C. in an incubator with 5% CO$_2$ for 20 hours. The compound was then prepared at 5-fold serial dilution to get 10 doses and 500 nL of each concentration was transferred to compound plate. Then 30 uL assay buffer (20 mM HEPES and 1× HBSS) was added to each well of compound plate; the plate was spin at 1500 rpm for 15 seconds. Then 20 uL of 2× Fluo-4 Direct™ No-wash Loading Buffer ((Invitrogen-F10471) was gently dispensed to each well of assay plate and was spin at 1000 rpm for 15 s, incubated at 37° C. for 50 min. The assay plate was removed from the incubator and placed at room temperature for 10 min. Then, the assay plate, compound plate and tip box were placed directly into the FLIPR Tetra® System. 10 uL compound was transferred from compound plate to the assay plate in FLIPR Tetra Fluorometric Imaging Plate Reader and plate was for 140 times; then calculated the "Max-Min" starting from Read 1 to 140 to generate the final signal for % Effect calculation; The data was analyzed using Prism, curve fitting equation "log(agonist) vs. response—Variable slope." Table 2 shows the results of these assays.

TABLE 2

| # | Compounds | Cell Assay (FLIPR Calcium) Kappa EC$_{50}$ (nM) |
|---|---|---|
| 1 | U-69593 | 46.93 |
| 2 | 5a | 2.64 |
| 3 | 5b | 9.7 |
| 4 | 7a | 6.86 |
| 5 | 7b | 3.76 |

As can be seen in Table 2, compound 5a provided improved cell assays over U-69596 as well as compounds 5b, 7a, and 7b. The response curve for compound 5a is shown in FIG. 1.

What is claimed is:

1. A compound of Formula (I) or a pharmaceutically acceptable salt thereof:

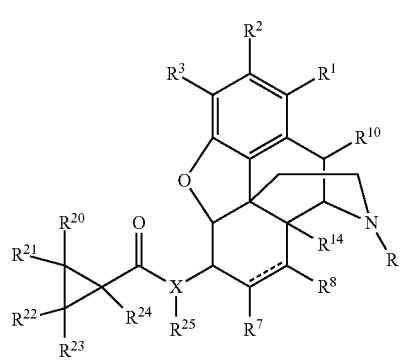

(I)

wherein:
R is hydrogen, methyl, allyl, cyclopropylmethyl, 1-hydroxylcyclopropylmethyl, or cyclobutylmethyl;
$R^1$ and $R^2$ independently are hydrogen, hydroxy, alkoxy, or aryloxy
$R^3$ is hydrogen, hydroxy, or alkoxy;
$R^7$ and $R^8$ independently are hydrogen, alkyl, or substituted alkyl;
$R^{10}$ is hydrogen, hydroxy, alkyoxy, or keto;
$R^{14}$ is hydrogen, hydroxy, or alkoxy;
one of $R^{20}$, $R^{21}$, $R^{22}$, and $R^{23}$ is heterocycle or substituted heterocycle and the rest are chosen from hydrogen or halogen, and $R^{24}$ is hydrogen;
$R^{25}$ is hydrogen, alkyl, substituted alkyl, aryl, substituted aryl, alkylaryl, substituted alkylaryl, heterocycle, or substituted heterocycle;
X is nitrogen; and
the dashed line represents an optional double bond.

2. The compound of claim 1, wherein the carbons attached to $R^{20}$-$R^{24}$ on the cyclopropyl ring independently have an R or S configuration.

3. The compound of claim 1, wherein heterocycle is chosen from furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, thienyl, phenol, or imidazopyridyl.

4. The compound of claim 1, wherein $R^3$ is hydroxy or $C_1$-$C_4$ alkyoxy; $R^7$ and $R^8$ are each hydrogen, $R^{14}$ is hydrogen or hydroxy; $R^{20}$, $R^{21}$, $R^{23}$, and $R^{24}$ are hydrogen, $R^{22}$ is furyl, thienyl, or 4-hydroxyphenyl; and $R^{25}$ is $C_1$-$C_4$ alkyl.

5. The compound of claim 1, wherein R is cyclopropylmethyl or 1-hydroxylcyclopropylmethyl; $R^3$ is hydroxy; $R^{14}$ is hydroxy; and $R^{25}$ is methyl.

6. The compound of claim 1, which has an optical activity of (−) or (+); and
carbons C-5, C-13, C-14, and C-9, respectively, have a configuration chosen from RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face of the molecule or the beta face of the molecule.

7. The compound of claim 1, wherein carbon C-6 has an alpha configuration or a beta configuration.

8. A pharmaceutical composition comprising a compound of claim 1 and at least one pharmaceutically acceptable excipient.

9. A method for treating a kappa opioid receptor-related disease or disorder, the method comprising administering a pharmaceutically effective amount of the pharmaceutical composition of claim 8 to an individual in need thereof;
wherein the kappa opioid receptor-related disease or disorder is pain, pruritis, or addiction.

10. The method of claim 9, wherein the addiction is substance abuse addiction.

11. The method of claim 9, wherein the pain is chronic pain, visceral pain, or neuropathic pain.

12. The method of claim 9, wherein the individual is a human.

* * * * *